United States Patent [19]

Bruns, Jr. et al.

[11] Patent Number: 5,567,715

[45] Date of Patent: Oct. 22, 1996

[54] METHODS OF TREATING DEPRESSION BY INHIBITING PHYSIOLOGICAL CONDITIONS ASSOCIATED WITH AN EXCESS OF NEUROPEPTIDE Y

[75] Inventors: Robert F. Bruns, Jr., Carmel; Donald R. Gehlert, Indianapolis, both of Ind.; J. Jeffry Howbert, Bellevue, Wash.; William H. W. Lunn, Indianapolis, Ind.

[73] Assignee: Eli Lilly and Company, Indianapolis, Ind.

[21] Appl. No.: 517,315

[22] Filed: Aug. 21, 1995

Related U.S. Application Data

[62] Division of Ser. No. 326,675, Oct. 20, 1994.

[51] Int. Cl.$^6$ .................... A61K 31/445; A61K 31/40
[52] U.S. Cl. .................... 514/324; 514/428; 514/448; 514/443; 514/578; 514/333; 514/422
[58] Field of Search .................... 514/324, 428, 514/443, 448, 578

[56] References Cited

U.S. PATENT DOCUMENTS

| | | | |
|---|---|---|---|
| 4,133,814 | 1/1979 | Jones et al. | 260/326.55 A |
| 4,380,635 | 4/1983 | Peters | 546/202 |
| 4,418,068 | 11/1983 | Jones | 424/267 |
| 5,075,321 | 12/1991 | Schreiber | 514/337 |

FOREIGN PATENT DOCUMENTS

| | | |
|---|---|---|
| 4311870A1 | 10/1994 | Germany. |
| WO93/10113 | 5/1993 | WIPO. |
| WO93/1074 | 6/1993 | WIPO. |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti-estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

Yang et al., "Raloxifene an Anti-Estrogen, Simulates the Effects of Estrogen in Inhibiting Bone Resorption Through Regulating TGFB-3 Expression in Bone;".Am Soc. for Bone and Min. Res., Tampa, Sep. 18–22, 1993.

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109;1981, 987–989.

Black, L. J. "Biological Actions and Binding Properites of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H-LY139481 Distribution In Vivo. Sixty–fifth Annual Meeting of the Endocrine Society, San Antonio, Texas, Jun. 8–10, 1983, abs. 93.

(List continued on next page.)

Primary Examiner—Theodore J. Criares
Attorney, Agent, or Firm—James J. Sales; David E. Boone

[57] ABSTRACT

A method of inhibiting a physiological disorder associated with an excess of neuropeptide Y or its symptoms comprising administering to a human in need thereof an effective amount of a compound having the formula $$R^1O\text{-[benzothiophene core]}-OR^3,\quad OCH_2CH_2-R^2 \quad (I)$$

wherein $R^1$ and $R^3$ are independently hydrogen, $-CH_3$, $$-\overset{O}{\underset{\|}{C}}-(C_1-C_6\,\text{alkyl}),\ \text{or}\ -\overset{O}{\underset{\|}{C}}-Ar,$$

wherein Ar is optionally substituted phenyl;

$R^2$ is selected from the group consisting of pyrrolidine, hexamethyleneamino, and piperidino; or a pharmaceutically acceptable salt of solvate thereof.

4 Claims, No Drawings

OTHER PUBLICATIONS

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22;1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF TREATING DEPRESSION BY INHIBITING PHYSIOLOGICAL CONDITIONS ASSOCIATED WITH AN EXCESS OF NEUROPEPTIDE Y

This application is a division of application Ser. No. 08/326,675 filed Oct. 20, 1994, abandoned.

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also presenm in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced about ten years ago from porcine brain as part of a general screening protocol to discover carboxy-terminal amidated peptides and was named neuropeptide Y due to its isolation form neural tissue and the presence of tyrosine as both the amino and carboxy terminal amino acid. Neuropeptide Y is a member of the pancreatic family of peptides and shares significant sequence homology with pancreatic polypeptide, and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main neurotransmitter criteria, since it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanine nucleotides, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind differnt fragments of neuropeptide Y and the closely related peptide YY. The Y1 receptor subtype appears to be the major vascular neuropeptide Y receptor. The Y2 receptor subtypes can also occur postjunctionally on vascular smooth muscle. The as-yet-unisolated Y3 receptor subtype appears to be neuropeptide Y-specific, not binding peptide YY. This receptor is likely to be present in the adrenal tissues, medulla, heart, and brain stem , among other areas. [For a review of neuropeptide Y and neuropeptide Y receptors, see, e.q., C. Wahlestedt and D. Reis, Annual Review of Pharmacology and Toxicology, 33:309–352 (1993)].

In view of the wide number of clinical maladies associated with an excess of neuropeptide Y, the development of neuropeptide Y receptor antagonists will serve to control these clinical conditions. The earliest such receptor antagonists were peptide derivatives. These antagonists proved to be of limited pharmaceutical utility because of their metabolic instability.

In essence, this invention provides a class of potent non-peptide neuropeptide Y receptor antagonists. By virtue of their non-peptide nature, the compounds of the present invention do not suffer from the shortcomings, in terms of metabolic instability, of known peptide-based neuropeptide Y receptor antagonists.

SUMMARY OF THE INVENTION

This invention encompasses methods for the treatment or prevention of a physiological disorder associated with an excess of neuropeptide Y, which method comprises administering to a mammal in need of said treatment an effective amount of a compound of Formula I

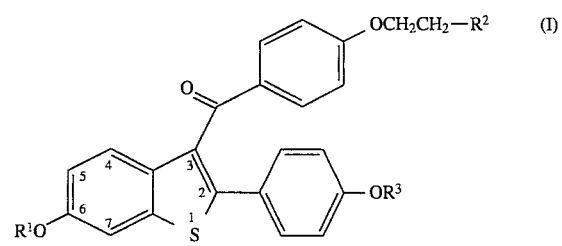

wherein $R^1$ and $R^3$ are independently hydrogen, —CH$_3$,

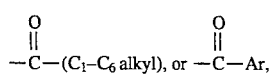

wherein Ar is optionally substituted phenyl;

$R^2$ is selected from the group consisting of pyrrolidino, hexamethyleneimino, and piperidino; and pharmaceutically acceptable salts and solyates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting a physiological disorder associated with an excess of neuropeptide Y.

The therapeutic and prophylactic treatments provided by this invention are practiced by administering to a human in need thereof a dose of a compound of formula I or a pharmaceutically acceptable salt or solvate thereof, that is effective to inhibit a physiological disorder associated with an excess of neuropeptide Y or its symptoms.

The term "inhibit" includes its generally accepted meaning which includes prohibiting, preventing, resraining, and slowing, stopping or reversing progression, severity or a resultant symptom. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosohoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit a physiological disorder associated with an excess of neuropeptide Y or its symptoms, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively treat or prevent the condition or symptom(s).

It is usually preferred to administer a compound of formula I in the form of an acid addition salt, as is customary in the administration of pharmaceuticals bearing a basic group, such as the piperidino ring. For such purposes the following oral dosage forms are available.

Formulations

In the formulations which follow, "Active ingredient" means a compound of formula I.

Formulation 1

Gelatin Capsules Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2

Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centstokes | 1.7 |

Formulation 3

Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4

Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formlation 5

Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6

Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7

Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8

Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The compounds of the present invention bind to receptors specific for neuropeptide Y as well as the closely related neuropeptides. [For a review of neuropeptide Y receptors, see, D. Gehlert, Life Sciences, 55:551–562 (1994)]. Receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13–36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. The Y-1 receptor is the only one that has been successfully cloned to date. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13–36 fragment, but interacts with the full length neuropeptide Y and peptide YY with equal affinity. C. Wahlestedt, et al., *Regulatory Peptides*, 13:307–318 (1986); C. Wahlestedt, et al., NEURONAL MESSENGERS IN VASCULAR FUNCTION, 231–241 (Nobin, et al., eds. 1987). Substitution of the amino acid at position 34 with a proline ($Pro^{34}$) results in a protein which is specific for the Y-1 receptor. E.K. Potter, et al., *European Journal of Pharmacology*, 193:15–19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC. [For a review, see, B.J. McDermott, et al., *Caordiovascular Research*, 27:893–905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., Proceedings of the National Academy of Sciences (U.S.A.), 89:5794–5798 (1992). The Y-1 receptor has been reported to couple to either second messenger system when studied using tissue preparations or cell lines naturally expressing te receptor. D. Gehlert, supra, at 553. The Y-1 receptor cannot, therefore, be distinguished solely on the basis of coupling to a single second messenger.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13–36), though the 3–36 fragment of neuropeptide Y and peptide YY provides improved affinity and selectivity. Y. Dumont, et al., *Society for Neuroscience Abstracts*, 19:726 (1993). Like Y-1 receptor, this receptor is coupled to the inhibition of adenylate cyclase, though in some preparations it may not be sensitive to pertussis toxin. The Y-2 receptor was found to reduce te intracellular levels of clacium in the synspse by selective inhibition of N-type calcium channels. Like the Y-1 receptor, te Y-2 receptor may exhibit differential coupling to second messengers.

The Y-2 receptors are found in a variety of brain regions, including the hippocampus, substantia nigralateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters.

Y-3 Receptor

This receptor is the newest and least studied of the established neuropeptide Y receptor subtypes. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F.P. Monnet, et al., *European Journal of Pharmacology*, 182:207–208 (1990).

The presence of this receptor is bestestablished in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al,, *Life Sciences*, 50:PL7–PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al., *Endocrinology*, 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to te crypt cells where intestinal chloride secretion is bleieved to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B.G. Stanley, et al., *Brain Research*, 604:30–317 (1993). While the pharmacology of this response resembled the Y-1 receptor, the 2–36 fragment of neuropeptide Y was significantly more potent than neuropeptide Y. In addition, intracerebroventricular neuropeptide Y(2–36) fully stimulates feeding, but does not reduce body temperature as does full length neuropeptide Y. F.B. Jolicoeur, et al,, *Brain Research Bulletin*, 26:309–311 (1991).

The biological activity of the compounds of the present invention was evaluated employing an initial screening assay which rapidly and accurately measured the binding of the tested compound to known neuropeptide Y receptor sites. Assays useful for evaluating neuropeptide Y receptor antagonists are well known in the art. See, e.g., U.S. Pat. No. 5,284,839, issued Feb. 8, 1994, which is herein incorporated by reference. See also, M.W. Walker, et. al., *Journal of Neurosciences*, 8:2438–2446 (1988).

Neuropeptide Y Binding Assay

The ability of the compounds of the instant invention were assessed as to their ability to bind to neuropeptide Y using a protocol essentially as described in M.W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at $-70°$ C.

The pellets were resuspended using a glass homogenizer in 25 mM HEPES (pH 7.4) buffer containing 2.5 mM calcium chloride, 1 mM magnesium chloride, and 2 mg/L bacitracin. Incubations were performed in a final volume of 200 µl containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 µM neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

| $R_1$ | Substitutions $R_2$ | $R_3$ | $IC_{50}$ (µM) $Y_1$ |
|---|---|---|---|
| $CH_3$ | 1-piperdine | H | ~12 |
| H | 1-hexamethylenimino | H | ~20 |
| H | 1-piperidine | H | ~10 |
| H | 1-piperidine | H | ~10* |
| H | 1-pyrrolidine | H | ~17 |
| H | 1-pyrrolidine | H | ~10* |

*hydrochloride salt

As the compounds of Formula I are effective neuropeptide Y receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders may include:
- disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;
- conditions related to increased sympathetic nerve activity for example, during or after coronary artery surgery, and operations and surgery in the gastrointestinal tract;
- cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;
- conditions related to pain or nociception;
- diseases related to abnormal gastrointestinal motility and secretion, such as different forms of ileus, urinary incontinence, and Crohn's disease;
- abnormal drink and food intake disorders, such as obesity, anorexia, bulimia, and metabolic disorders;
- diseases related to sexual dysfunction and reproductive disorders;
- conditions or disorders associated with inflammation;
- respiratory diseases, such as asthma and conditions related to asthma and bronchoconstriction; and
- diseases related to abnormal hormone release, such as leutinizing hormone, growth hormone, insulin, and prolactin.

We claim:

1. A method of inhibiting a physiological disorder associated with an excess of neuropeptide Y, comprising administering to a human in need thereof an effective amount of a compound having the formula

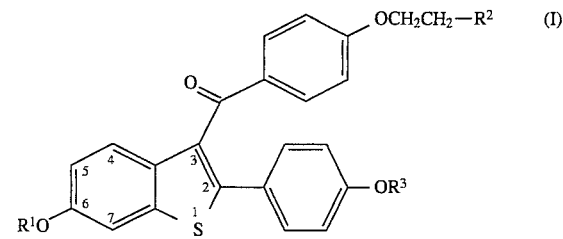

wherein $R^1$ and $R^3$ are independently hydrogen, —CH3,

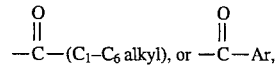

wherein Ar is optionally substituted phenyl;

$R^2$ is selected from the group consisting of pyrrolidine, hexamethyleneimino, and piperidino; or a pharmaceutically acceptable salt of solvate thereof, wherein the condition associated with an excess of neuropeptide Y is depression.

2. The method of claim 1 wherein said compound is the hydrochloride salt thereof.

3. The method of claim 1 wherein said administration is prophylactic.

4. The method of claim 1 wherein said compound

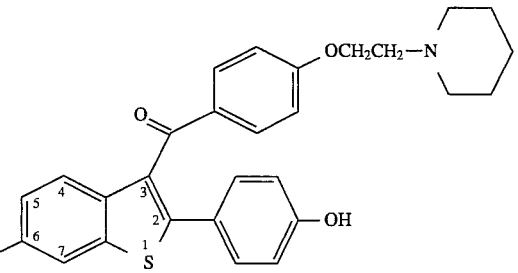

or its hydrochloride salt.

* * * * *